United States Patent [19]

Engelman

[11] 4,444,203
[45] Apr. 24, 1984

[54] INTRAVENOUS CATHETER PLACING AND SPECIMEN GATHERING DEVICE

[75] Inventor: Allan Engelman, Walla Walla, Wash.

[73] Assignee: Lab-A-Cath, Inc., Hermiston, Oreg.

[21] Appl. No.: 362,319

[22] Filed: Mar. 26, 1982

[51] Int. Cl.³ .............................................. A61B 5/00
[52] U.S. Cl. .................................. 128/764; 128/763
[58] Field of Search ............... 128/760, 763, 764, 767, 128/768, 770

[56] References Cited

U.S. PATENT DOCUMENTS

| | | | |
|---|---|---|---|
| 3,063,451 | 11/1962 | Kowalk | 128/763 |
| 3,459,183 | 8/1969 | Ring et al. | 128/763 |
| 3,585,984 | 6/1971 | Buchanan | 128/764 |
| 3,648,684 | 3/1972 | Barnwell et al. | 128/764 |
| 3,714,945 | 2/1973 | Stanley | 604/164 |
| 3,734,080 | 5/1973 | Petterson et al. | 128/764 |
| 3,752,510 | 8/1973 | Windischman et al. | 604/283 X |
| 3,817,240 | 6/1974 | Ayres | 128/764 |
| 4,073,297 | 2/1978 | Kopp | 604/164 |
| 4,193,400 | 3/1980 | Loveless et al. | 604/168 |
| 4,269,186 | 5/1981 | Loveless et al. | 604/168 |

Primary Examiner—Kyle L. Howell
Assistant Examiner—Christine A. Fukushima
Attorney, Agent, or Firm—Wells, St. John & Roberts

[57] ABSTRACT

An intravenous catheter insertion set and blood sample gathering unit are combined to allow catheterization for intravenous medication and gathering of blood samples from the same venipuncture site. A hypodermic needle and a vacuum container needle protrude in opposite directions from a hub. A catheter is carried by the hypodermic needle. The hub includes a flashback chamber, vented to allow blood to flow into view within the chamber following proper venipuncture. The vent is selectively sealed as the plug end of a vacuum container is pierced by the vacuum container needle. Blood is then drawn into the tube by vacuum pressure. When a sufficient sample has been taken, the needle assembly is withdrawn, leaving the catheter in place.

16 Claims, 5 Drawing Figures

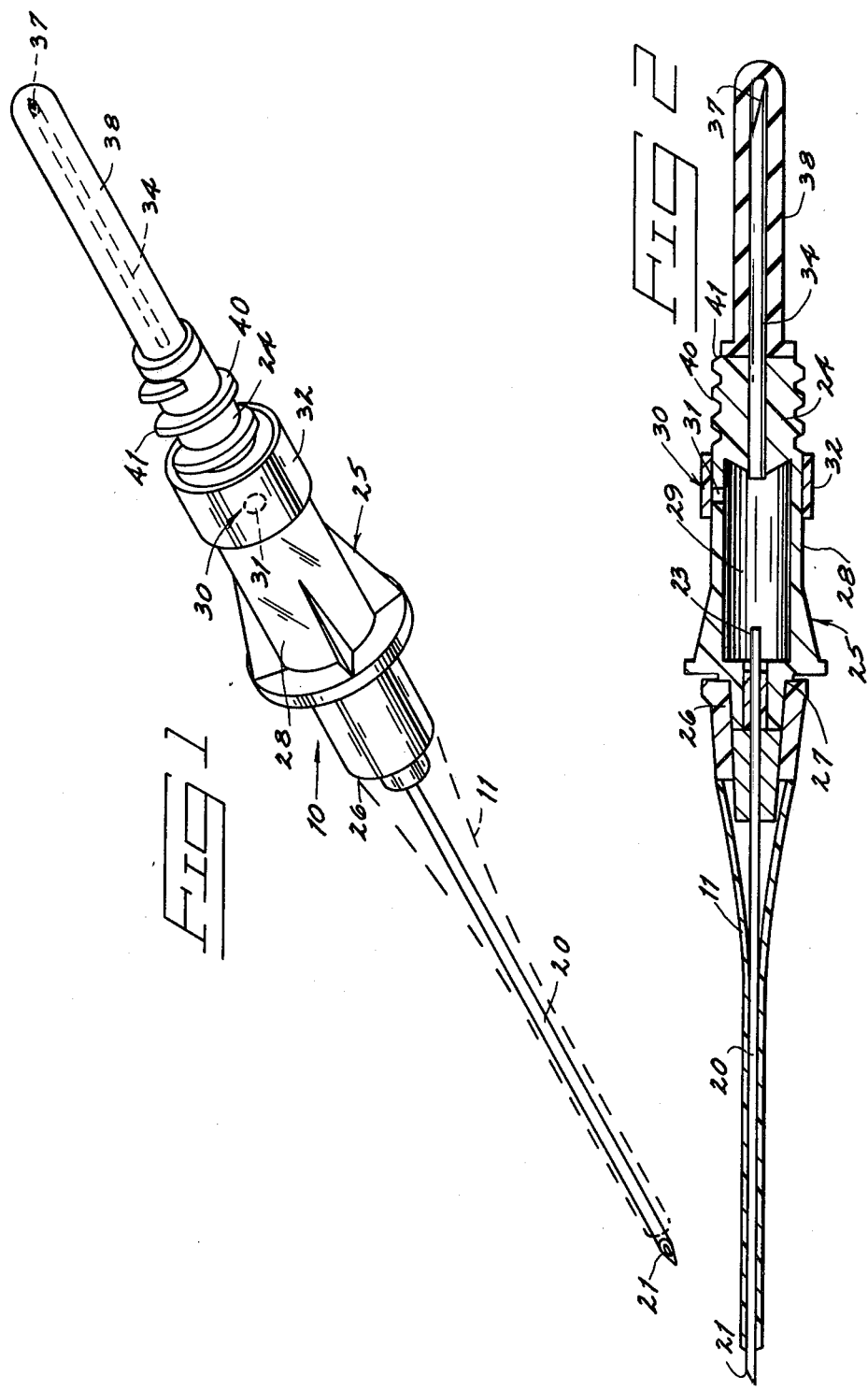

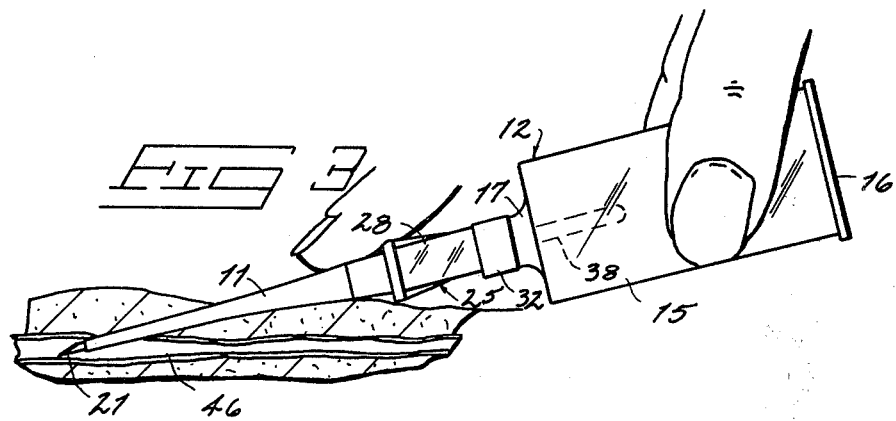
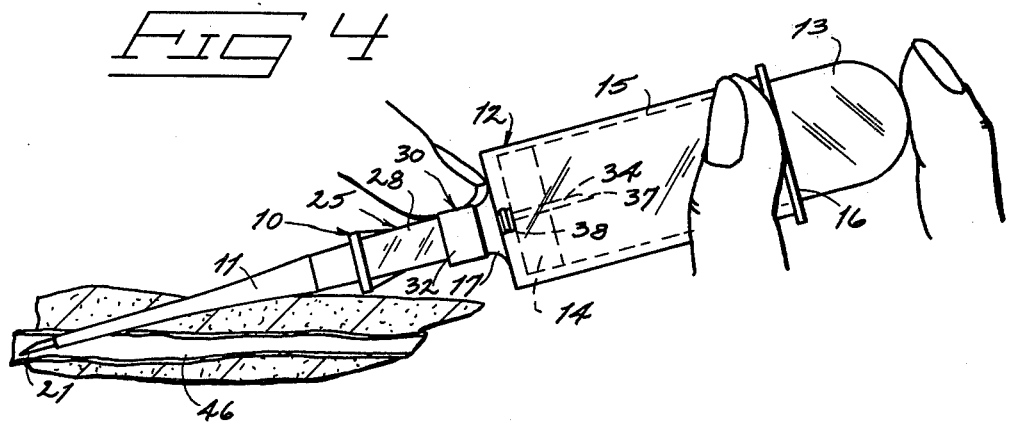
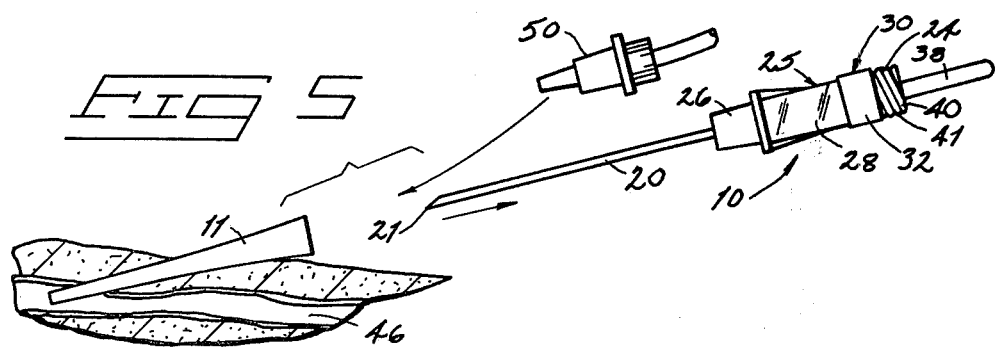

INTRAVENOUS CATHETER PLACING AND SPECIMEN GATHERING DEVICE

FIELD OF THE INVENTION

The present invention relates to hypodermic needle sets for establishing an intravenous catheter and allowing for the taking of a blood sample from the same venipuncture.

BACKGROUND

A patient often goes into shock when having a traumatic medical problem. When this happens, blood pressure drops rapidly and blood vessels tend to deflate or collapse all together. The importance of establishing access to the circulatory system through a blood vessel for volume control and administration of medication is second only to establishing the airway. In many cases, these steps are performed simultaneously.

It is also very important for a proper data base line on blood chemistry that blood samples be taken prior to administration of intravenous medication. However, in emergency situations, immediate attention must be devoted to revival or life sustaining measures. Lab work is either forgotten or time is not taken to acquire samples. Later a blood sample may become difficult to obtain since peripheral vessels may have collapsed, making a venipuncture impossible. Also, intravenous medications started earlier often render any later sample useless.

Intravenous administration of fluids is started with a flexible catheter slidably mounted over an elongated hypodermic needle. The needle adds rigidity to the otherwise flexible catheter. The needle hub may include a "flashback" chamber and vented plug (as shown in U.S. Pat. Nos. 4,269,186 and 4,193,400) to allow blood flow back through the needle and into the chamber, thereby indicating proper venipuncture. The needle hub and plug can be removed as the needle is withdrawn, after establishing "flashback", to allow mounting of a flexible supply tube to the catheter.

It is conventional today to take blood samples through a double ended needle assembly. One needle establishes venipuncture and delivers blood to second coaxial needle. The second needle is often covered by a rubber sleeve to stop free blood flow. A central hub between the needles is threaded for connection to a rigid container guide with the sleeve-covered second needle projecting into its interior. A rubber plugged specimen container may then be inserted into the guide and pressed against the second needle, which penetrates the sleeve and plug. The outer needle end is exposed to negative pressure within the container. Blood is thereby drawn through the inter-connected needles and into the specimen container. When enough blood has been drawn, the container is pulled free. The rubber sleeve again seals the needle. The rubber plug also closes to seal the container and blood specimen contained therein. The process can be repeated with successive specimen containers for as many specimens as required. This specimen gathering technique is effective, but must be performed as a separate function from intravenous catheterization.

Combining the functions of a specimen gathering needle and an intravenous catheterization has been previously attempted by using an intravenous catheterization set and a specially adapted syringe on the catheter needle hub. The catheter and needle are inserted in the usual manner. However, since there is no available "flashback" chamber, the only way to verify successful venipuncture is to aspirate the syringe. If there has been no venipuncture, no blood will appear in the syringe barrel and repositioning of the needle is necessary.

Combining conventional intravenous catheter sets having flashback chambers with an aspirator syringe at first glance appears to be a solution to the problem. However, in actual practice such a simple combination cannot function, since the syringe requires a hermetic seal between the syringe barrel and the patient's bloodstream. This conflicts with the necessity of the flashback chamber being vented to the atmosphere in order for the catheter set to properly function (see U.s. Pat. Nos. 4,269,186 and 4,193,400). The need remains today to safely and efficiently combine the function of an intravenous catheter and a blood specimen container system to gain the advantage of acquiring undiluted blood specimens without substantially interfering with or delaying application of intravenous fluids.

BRIEF DESCRIPTION OF THE DRAWINGS

A preferred form of the present invention is illustrated in the accompanying drawings in which:

FIG. 1 is a pictorial view of the present needle;

FIG. 2 is a longitudinal section of the needle;

FIG. 3 is a diagrammatic view showing insertion with a tube holder attached to the needle;

FIG. 4 is a diagrammatic view showing placement of a vacuum container for gathering a specimen; and FIG. 5 is a diagrammatic view showing removal of the present needle and vacuum tube assembly, and connection of an intravenous supply tube.

DETAILED DESCRIPTION

The following disclosure is submitted in compliance with the constitutional purposes of the Patent Laws "to promote the progress of science and useful arts" (Article 1, Section 8).

A needle assembly of the present invention is generally designated by the numeral 10 in the accompanying drawings. The needle assembly 10 enables placement of an intravenous catheter 11 while also facilitating blood sampling via a removable blood sample assembly 12. The present invention is therefore useful both for starting intravenous procedures and for obtaining blood specimens.

The blood sample assembly 12 may be comprised of a standard vacuum container 13 (FIG. 4) slidably received within a standard container guide 15. The vacuum container 13 is sealed by a resilient plug 14 and includes a hollow evacuated chamber. The guide 15 includes an open first end 16 that slidably receives the container 13 and plug 14. A second end 17 of the guide is threaded for mounting to the needle assembly 10. The container and guide are commercially available units known in the trade as "Vacutainer" TM components, produced by Becton & Dickensen Co. of Rutherford, N.J. 07070.

The present needle assembly 10 as shown in FIGS. 1 and 2 includes an elongated hypodermic needle 20. The needle includes a hollow core extending from a pointed end 21 to a base end 23 (FIG. 2). The point at end 21 is formed by a relatively flat planar point surface formed along an inclined plane, facing one side of the needle assembly. The base end 23 of the hypodermic needle 20 is mounted to a hub 25.

The hub 25 is preferably formed of a clear plastic material that is somewhat elongated and includes an end 26 mounting the needle base end 23. A catheter receiving surface 27 is located at hub end 26 to mount the base end of the catheter 11. The hypodermic needle shank receives and slidably supports the remaining reduced end of the catheter in the manner shown in FIGS. 1 and 2.

The hub 25 includes a transparent peripheral wall 28 forming an enclosed flashback chamber 29 (FIG. 2) openly communicating with the hollow core of needle 20. The flashback chamber receives blood after venipuncture by the needle 20 to indicate that proper venipuncture has been accomplished.

A vent means 30 is formed through the hub and into the flashback chamber 29 in order to selectively vent air from the flashback chamber and allow flow of blood into the flashback chamber following proper venipuncture. The vent means 30 may be comprised of a vent hole 31 formed through the transparent wall 28. Some form of one way valve means or cover 32 may be supplied to selectively allow fluid (air) to flow from the flashback chamber 29. Manual pressure against the cover will seal the vent hole 31 and prevent air from being drawn through it and into the chamber 29. A flexible cover sleeve is shown in the drawings for this purpose. However, it is to be understood that other known forms of valves, such as one-way flap valves, could be used as well to allow ventilation of the chamber while preventing reverse flow through vent hole 31 and resulting contamination of fluids contained therein.

It is preferred that the vent hole 31 open to the same side as the planar surface of the needle point 21. Since hypodermic needles are typically inserted with the point surfaces facing outwardly, the vent hole 31 will then be automatically positioned for easy access by the attendant's finger (see FIG. 4).

An opposite end 24 of the hub 25 mounts the base end of a vacuum tube needle 34. The vacuum tube needle includes a hollow core openly communicating with the flashback chamber 29. Needle 34 extends opposite to the hypodermic needle 20, preferably along the same axis, to a pointed end 37. A resilient sleeve 38 may be received over the length of needle 34, covering the pointed end 37.

A vacuum container guide mount 40 is provided on the hub end 24 to receive the complementary threaded fitting at the guide end 17. Threads 41 may be provided coaxially with the needle 34, arranged so the needle 34 will be received and situated within the guide 15 when it is threaded onto the hub 25. This arrangement is shown in FIGS. 3 and 4.

It is contemplated that the present invention be produced and marketed as the needle arrangement shown in FIG. 1 or in a kit form including the container guide 15 and one or more vacuum containers 13. Furthermore, the present invention can be made and distributed with or without a catheter 11 situated in place over the hypodermic needle 20.

Prior to operation, the catheter 11 is secured over the hypodermic needle 20 so that the enlarged base end of the catheter 11 rests against the catheter receiving surface 27 of the hub 25. The opposite, reduced end of the catheter 11 is slidably positioned over the hypodermic needle 20 adjacent its pointed end 21.

At this point, the hypodermic needle 20 and catheter may be inserted. The needle is forced through tissues until the pointed end 21 pierces and enters into a vessel 46 (FIG. 3), thus establishing venipuncture.

This step may be accomplished with or without the container guide 15 being mounted in place on the mount 40. It is preferably located on the mount, however, since it is desirable to minimize movement of the pointed needle end 21 once it has been situated within the blood vessel. Accidental undesired movement can endanger the tissues areas adjacent the sharp needle end 21. Furthermore, the holder 15 provides a convenient gripping surface to facilitate handling of needle 20 during the insertion process.

As venipuncture is achieved, blood within the associated vessel 46 is allowed to enter the flashback chamber 29. Air within the flashback chamber is displaced through the vent means 30. It is pointed out that the air will pass outwardly through the vent hole 31 and between the hub and cover 32 relatively freely as blood is received within the chamber. The cover 32 allows air to escape, but does not leave the vent hole 31 exposed. The blood sample passing through the chamber will therefore remain uncontaminated.

Once the "flashback" of blood within the chamber 29 becomes apparent, one or more samples may be taken using vaccum containers 13. FIG. 4 illustrates the positioning of the vacuum container 13 for collection of a blood sample. The resilient plug 14 at the end of the vacuum container 13 is inserted through the open holder end 16. The container 13 is then moved toward the needle 34 and resilient sleeve 38. As plug 14 comes into contact with sleeve 38, further axial force will cause the pointed needle end 37 to penetrate the sleeve and plug. The resilient sleeve 38 will compress along the length of the needle as the plug is forced axially down to the reduced base end of the holder (FIG. 4). When the pointed needle end 37 extends fully through the plug 14, vacuum pressure within the container 13 will draw blood through the needle 34 and into the container 13.

During this time, finger pressure may be applied to the cover 32 directly over the vent hole 31 to prevent air from being drawn into the flashback chamber 29. Alternatively, other one-way valves might be utilized that would not require manual manipulation to prevent seepage of air into chamber 29.

The chamber 13 is withdrawn from the guide 15 when a sufficient amount of blood has been drawn. As this is done, the resilient sleeve 38 returns to its original configuration and closes around the pointed end 37 of needle 34 as the plug 14 becomes disengaged. The puncture hole from the needle in the plug 14 is also sealed as the resilient plug material returns to its original configuration. Additional vacuum containers can then be used to collect further blood samples as desired. The collection process is repeated in the same manner as described above.

Once collection of a desired number of blood samples is completed, the entire unit with the exception of the catheter 11 can be withdrawn to facilitate connection with an intravenous tube connector 50 as generally shown in FIG. 5.

It is pointed out that a single insertion is required for both placement of the catheter and accessing an appropriate vessel for blood samples. The time required to collect the blood sample is substantially diminished due to the convenience of combining insertion of the catheter with the sampling structure. Collection of the sample at the earliest possible stage, prior to application of intravenous fluids, is made possible.

In compliance with the statute, the invention has been described herein in more or less specific language as to structural features. It is to be understood, however, that it is not intended to limit the invention to the specific features shown. The means and construction herein disclosed exemplify a preferred form of putting the invention into effect. The invention is therefore restricted in any form or modification thereof by the scope of the appended claims, appropriately interpreted in accordance with the doctrine of equivalents.

I claim:

1. A needle assembly for placing an intravenous catheter and facilitating blood sampling by a vacuum container specimen gathering device, said assembly comprising:

an elongated hypodermic needle having a hollow core extending from a pointed end to a base end;

an intravenous catheter releasably mounted about said hypodermic needle;

a hub member mounting the needle in fixed relation thereto at the needle base end and including a flashback chamber defined by a transparent hub wall, said chamber openly and directly communicating with the hollow core of the hypodermic needle for receiving and visibly displaying blood received through the hypodermic needle core following venipuncture by the pointed needle end;

a vent hole formed through the hub wall and opening directly into the flashback chamber for selectively venting air from the flashback chamber into the atmosphere; and vacuum container needle means mounted to the hub in fixed relation thereto and having an open bore opening directly into the flashback chamber for penetrating a vacuum container specimen gathering device and delivering blood into the vacuum container specimen gathering device in response to the vacuum pressure within the container after venipuncture by the hypodermic needle.

2. The needle assembly of claim 1 further comprising a resilient sleeve fitted over the vacuum container needle, said sleeve being penetrable by the vacuum container needle.

3. The needle assembly of claim 1 wherein the pointed end of the hypodermic needle is formed along a substantially planar point surface facing to one side of the needle and wherein the vent hole opens into the chamber from the same side of the assembly as the planar point surface of the hypodermic needle to indicate angular orientation of the planar point surface following subcutaneous insertion thereof.

4. The needle assembly of claim 1 further comprising a one-way valve on the hub and communicating with the chamber through the vent hole for allowing escape of air from the chamber and selectively preventing seepage of air back into the chamber.

5. A needle assembly for placing an intravenous catheter and facilitating blood sampling by a vacuum container specimen gathering device and vacuum container guide, said assembly comprising:

an elongated hypodermic needle having a hollow core extending from a pointed end to a base end;

a hub member mounting the hypodermic needle in fixed relation thereto at the needle base end and including a flashback chamber defined by a transparent hub wall, said chamber openly and directly communicating with the hollow core of the hypodermic needle for receiving and visibly displaying blood received through the hypodermic needle core following venipuncture by the pointed needle end;

an intravenous catheter receiving surface on the hub for receiving and releasably mounting an intravenous catheter;

a vent hole formed through the hub into the flashback chamber for selectively venting air from the flashback chamber to the atmosphere;

a mount on the hub member for releasably securing a vacuum container guide to the hub member; and a vacuum container needle means mounted to the hub in fixed relation thereto and having an open bore opening directly into the flashback chamber adjacent the mount, for penetrating the vacuum container to deliver blood into the vacuum container in response to vacuum pressure within the container after venipuncture by the hypodermic needle.

6. The needle assembly of claim 5 further comprising a resilient sleeve fitted over the vacuum container needle, said sleeve being penetrable by the vacuum container needle.

7. The needle assembly of claim 5 wherein the pointed end of the hypodermic needle is formed along a substantially planar point surface facing to one side of the needle and wherein the vent hole opens into the flashback chamber from the same side of the assembly as the planar point surface of the hypodermic needle to thereby indicate the orientation of the planar point surface following subcutaneous insertion thereof.

8. The needle assembly of claim 5 further comprising a one-way valve on the hub and communicating with the flashback chamber through the vent hole for allowing escape of air from the flashback chamber into the atmosphere and selectively preventing seepage of air back into the flashback chamber.

9. An intravenous catheterization and blood sampling kit, comprising:

an elongated tubular hypodermic catheter needle with an open hollow core extending from a base end to a pointed end;

a hub fixedly mounting the catheter needle base end and defining a flashback chamber directly and openly communicating with the catheter needle core and having a transparent viewing wall, for receiving blood from the catheter needle following venipuncture by the pointed catheter needle end;

a vent hole formed through the viewing wall of the flashback chamber opening into the chamber to permit passage of fluid from the chamber;

an elongated catheter releasably received over the catheter needle and having a reduced end slidably engaging the catheter needle near the pointed catheter needle end and an enlarged end releasably received by the hub;

a vacuum container needle affixed to the hub and projecting in a direction opposite the catheter needle from the hub and having a hollow core opening directly into the flashback chamber, and leading from the hub to a pointed end;

a vacuum container formed of a hollow tube sealed by a resilient plug; and vacuum container guide means for slidably receiving the vacuum container, plug first, through an open first end and having an opposite axially spaced second end to be removably secured to the hub with the vacuum container needle projecting into the guide means in the path of the resilient plug, for guiding the vacuum container axially in relation to the vacuum container needle.

10. An intravenous catheter and vacuum tube blood sample needle, comprising:
- a hollow substantially cylindrical hub, enclosing a flashback chamber having a transparent peripheral wall;
- a vent hole formed through the hub and opening into the chamber for directly venting the flashback chamber to the atmosphere; and
- needles immovably affixed to and projecting in opposite directions from the hub, both having hollow cores opening directly into the flashback chamber.

11. The intravenous catheter and vacuum tube blood sample needle of claim 10 wherein one of the needles is an elongated intravenous needle with a point at one end formed by an inclined point surface; and
- wherein the vent hole includes a vent hole opening on the same side of the hub as the inclined point surface on the intravenous needle.

12. The intravenous catheter and vacuum tube blood sample needle of claim 10 wherein one of the needles is a vacuum container needle and further comprising a resilient sleeve slidably received over the vacuum container needle, penetrable by and axially collapsible over the vacuum container needle.

13. The intravenous catheter and vacuum tube blood sample needle of claim 10 further comprising a catheter receiving surface on one end of the hub adjacent one of the needles.

14. The intravenous catheter and vacuum tube blood sample needle of claim 13 further comprising a vacuum container guide mount at a remaining end of the hub adjacent the remaining needle.

15. The intravenous catheter and vacuum tube blood sample needle of claim 10 wherein the needles are coaxial and wherein the vent hole is formed through the transparent peripheral wall transverse to the coaxial needle axes.

16. The intravenous catheter and vacuum tube blood sample needle of claim 10 further comprising;
- valve means on the hub for selectively allowing escape of air from within the flashback chamber through the hole and for selectively sealing the chamber against air entering through the hole.

* * * * *